United States Patent [19]

Harder et al.

[11] 4,436,668
[45] Mar. 13, 1984

[54] PREPARATION OF CARBONATES

[75] Inventors: Wolfgang Harder, Weinheim; Franz Merger, Frankenthal; Friedrich Towae, Ludwigshafen, all of Fed. Rep. of Germany

[73] Assignee: BASF Aktiengesellschaft, Ludwigshafen, Fed. Rep. of Germany

[21] Appl. No.: 267,763

[22] Filed: May 28, 1981

[51] Int. Cl.³ ............................................. C07C 68/00
[52] U.S. Cl. .................................................. 260/463
[58] Field of Search ........................................ 260/463

[56] References Cited

U.S. PATENT DOCUMENTS 2,834,799  5/1958  Sowa ................................. 260/463
4,331,610  5/1982  Heitz et al. ........................ 260/463

OTHER PUBLICATIONS

N. Gaylord, Journal of Organic Chemistry, vol. 25, pp. 1874–1876(1960). Reactions of Disubstituted Carbamates with Alcohols.

P. Smith, Chemistry of Open-Chain Nitrogen Compounds, vol. 1, p. 261, Benjamin, Inc., NY 1965.

M. Groenvald et al., Acta. Chem. Scand. 14, 1374–1380(1960).

*Primary Examiner*—Mary C. Lee
*Assistant Examiner*—M. C. Eakin
*Attorney, Agent, or Firm*—John H. Shurtleff

[57] ABSTRACT

Carbonates are prepared by reacting carbamic acid esters with alcohols at above 140° C., the ammonia formed being stripped from the reaction mixture during the reaction by passing an inert gas or vapor therethrough.

The carbonates obtainable by the process of the invention are valuable starting materials for the preparation of dyes, crop protection agents and plastics.

12 Claims, No Drawings

PREPARATION OF CARBONATES

The present invention relates to a novel process for the preparation of carbonates by reacting carbamic acid esters with alcohols at above 140° C., the ammonia formed being removed during the reaction.

At the present time, the processes used to prepare dialkyl carbonates are in the main the following: (a) Phosgenation of alcohols (Houben-Weyl, Methoden der org. Chemie, volume VIII, pages 105 and 106), (b) Alcoholysis of alkylene carbonates (German Published Application DAS No. 2,615,665) and (c) Oxidative carbonylation of alcohols (German Published Application DAS No. 2,743,690 and German Laid-Open Applications DOS No. 2,437,133 and DOS No. 2,334,736).

All these processes suffer from severe disadvantages. Thus, preparation by process (a) entails a complicated and expensive technology, because of the high toxicity of the phosgene used. Process (b) is operationally and economically unfavorable, since the production of the dialkyl carbonate always entails the simultaneous production of a stoichiometric amount of glycol. Process (c) requires expensive technology for handling carbon monoxide under pressure. In addition, the problem of the recycling, and the corrosiveness, of the Cu salts employed as catalysts presents considerable difficulties in industrial operation.

U.S. Pat. No. 2,834,799 describes the preparation of dialkyl carbonates from carbamic acid esters and alcohol in the presence of not less than a stoichiometric amount of boron trifluoride. Disadvantages of this process are the use of stoichiometric amounts of boron trifluoride and the removal of the $NH_3$-$BF_3$ adduct necessarily formed during the reaction, and these stand in the way of a simple industrial process of preparation. The preparation of dialkyl carbonates from urea via carbamic acid esters which are reacted with alcohols without the addition of a stoichiometric amount of an acid such as $BF_3$ has hitherto appeared impossible (Houben-Weyl, Methoden der org. Chemie, volume VIII, pages 105 to 106).

We have found that carbonates of the formula I

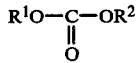   I where $R^1$ and $R^2$ may be identical or different and each is an aliphatic, cycloaliphatic or araliphatic radical, are obtained in an advantageous manner by reacting a carbamic acid ester with an alcohol, if a carbamic acid ester of the formula II

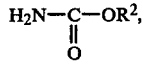   II where $R^2$ has the above meanings, is reacted with an alcohol of the formula III

   III, where $R^1$ has the above meanings, at above 140° C., the ammonia formed being removed during the reaction.

Further, we have found that the reaction is advantageously carried out in the presence of a tertiary amine or amidine as the catalyst.

We have also found that the reaction is advantageously carried out in the presence of a compound of a metal chosen from the elements of groups Ia, Ib, IIa, IIb, IIIa, IIIb, IVa, IVb, Va, Vb, VIb, VIIb and VIIIb of the periodic table.

Where methyl carbamate and methyl alcohol are used, the reaction can be represented by the following equation:

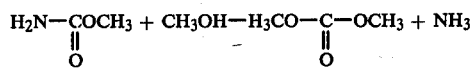

Compared to the conventional processes, the process according to the invention gives a large number of carbonates more simply and more economically, and in good yield and high purity. Involved isolation, detoxication and working-up procedures, operation with toxic materials such as phosgene and carbon monoxide, and corrosion problems, are all avoided.

All these advantageous aspects of the process according to the invention are surprising in view of the prior art. Furthermore, effective catalysis of the carbonate formation would specifically not have been expected by using tertiary amines or metal compounds in place of carrying out a stoichiometric reaction with the strong Lewis acid $BF_3$.

The starting material II is reacted with the starting material III in stoichiometric amount or in an excess or deficiency; advantageously, from 0.9 to 50 moles, especially from 2 to 10 moles, of starting material III are employed per mole of starting material II. Preferred starting materials II and III, and accordingly preferred end products I, are those where $R^1$ and $R^2$ may be identical or different and each is aralkyl of 7 to 12 carbon atoms, alkenyl of 2 to 12, advantageously of 2 to 6, carbon atoms and preferably having one double bond, cycloalkyl of 5 to 8 carbon atoms or, in particular, alkyl of 1 to 18, advantageously 1 to 12, more especially 1 to 8, carbon atoms. The above radicals can additionally be substituted by groups which are inert under the reaction conditions, for example by alkyl or alkoxy, each of 1 to 4 carbon atoms.

Examples of suitable starting materials II are the esters of carbamic acid with methanol, ethanol, propanol, iso-propanol, sec.-butanol, iso-butanol, n-butanol, n-pentanol, tert.-amyl alcohol, pentan-2-ol, pentan-3-ol, isoamyl alcohol, n-hexanol, hexan-2-ol, n-heptanol, heptan-2-ol, 2- and 3-methylhexanol, 2- and 3-ethylhexanol, n-octanol, octan-2-ol, n-nonanol, n-decanol, benzyl alcohol, 2-phenylethanol, lauryl alcohol, allyl alcohol, ethylene glycol monomethyl ether, ethylene glycol monoethyl ether, ethylene glycol monobutyl ether, ethylene glycol monoethoxyethyl ether, cyclohexanol and cyclopentanol. The esters of methanol, ethanol, propanol, butanol, pentanol and hexanol are particularly preferred.

Examples of suitable starting materials III are methanol, ethanol, propanol, iso-propanol, sec.-butanol, iso-butanol, n-butanol, n-pentanol, tert.-amyl alcohol, pentan-2-ol, pentan-3-ol, isoamyl alcohol, n-hexanol, hexan-2-ol, n-heptanol, heptan-2-ol, 2- and 3-methylhexanol, 2- and 3-ethylhexanol, n-octanol, octan-2-ol, n-nonanol, n-decanol, benzyl alcohol, 2-phenylethanol, lauryl alcohol, allyl alcohol, ethylene glycol monomethyl ether, ethylene glycol monoethyl ether, ethylene glycol monobutyl ether, ethylene glycol monoethoxyethyl ether, cyclohexanol and cyclopentanol. Methanol, ethanol, propanol, butanol, pentanol and hexanol are particularly preferred.

The reaction is carried out at above 140° C., in general at from 140° to 260° C., preferably from 140° to 230° C., especially from 160° to 220° C., under atmospheric or superatmospheric pressure, preferably from 0.1 to 60 bar, continuously or batchwise. Advantageously, the pressure is chosen so that the alcohol and/or the solvent, if any, refluxes at the reaction temperature. Advantageously, the reaction mixture itself serves as the solution medium or suspension medium. In such cases it is at times advantageous to add an excess of starting material III from the very start. If desired, solvents which are inert under the reaction conditions can be employed; those in which ammonia is only slightly soluble are advantageous. Examples of suitable solvents are aromatic hydrocarbons, eg. toluene, ethylbenzene, o-, m- and p-xylene, isopropylbenzene, methylnaphthalene, mesitylene, chlorobenzene, o- and m-dichlorobenzene, o-, m- and p-chlorotoluene and 1,2,4-trichlorobenzene; ethers, eg. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol monomethyl ether, tetrahydrofuran, dioxane and $\beta,\beta'$-dichlorodiethyl ether; aliphatic or cycloaliphatic hydrocarbons, eg. heptane, nonane, gasoline fractions boiling within the range from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane, octane pentane, 2-methylbutane, cyclopentane, n-hexane, isooctane, n-decane, n-undecane, n-dodecane, n-hexadecene and n-octadecane; cyclosiloxanes, eg. octamethylcyclotetrasiloxane, decamethylcyclopentasiloxane, dodecamethylcyclohexasiloxane, tetradecamethylcycloheptasiloxane and hexadecamethylcyclooctasiloxane; carbon tetrachloride and carbon disulfide; and mixtures of the above. The solvent is preferably used in an amount of from 50 to 2,000% by weight, advantageously from 100 to 200% by weight, based on starting material III.

In a preferred embodiment, the catalyst used is a tertiary amine or an amidine, advantageously in an amount of from 0.0001 to 1, preferably from 0.005 to 0.5, especially from 0.01 to 0.1, equivalent of amino or amidine group in the molecule, per mole of starting material II. Mixtures of the said catalysts can also be employed in the reaction. The amine can be a monoamine, diamine or polyamine. Suitable catalysts include trimethylamine, triethylamine, tripropylamine, triisopropylamine, tributylamine, triisobutylamine, tri-sec.-butylamine, tribenzylamine, tricyclohexylamine, trihexylamine, dimethylhexylamine, methyldiisopropylamine, tetramethylethylenediamine, tetramethyltetramethylenediamine, tetramethylhexamethylenediamine, tetramethylneopentyldiamine, dimethylethylamine, dimethyllaurylamine, N,N-dimethylaniline, N,N-diethylaniline, N,N-dimethyltoluidine, pyridine, $\alpha$-, $\beta$- and $\gamma$-picoline, quinoline, isoquinoline, quinazoline, quinoxaline, p-dimethylaminopyridine, p-diethylaminopyridine, p-pyrrolidinopyridine, N-methylimidazole, N-methylpyrrolidine, 1,4-diazabicyclo-[2,2,2]-octane, 1,3-diazabicyclo-[5,4,0]-undecene and 1,5-diazabicyclo-[4,3,0]-nonene. Polymers which contain tert.-amino groups, for example 4-polyvinylpyridine and poly-N-vinylimidazole, can also be used. Triethylamine, tripropylamine, tributylamine, tetramethylethylenediamine, tetramethylpropylenediamine, tetramethyltetramethylenediamine, tetramethylpentamethylenediamine, tetramethylhexamethylenediamine, tetramethylneopentyldiamine, p-dimethylaminopyridine, p-pyrrolidinopyridine, 1,4-diazabicyclo-[2,2,2]-octane, 1,5-diazaobicyclo-[4,3,0]-nonene and 1,3-diazabicyclo-[5,4,0]-undecene are particularly advantageous.

In a further preferred embodiment, a compound of a metallic element of one of the groups mentioned above is used as the catalyst. The periodic table referred to is as given in D'Ans-Lax, Taschenbuch für Chemiker und Physiker (Springer, Berlin, 1967), volume 1, page 53, corresponding to Weast, Handbook of Chemistry and Physics (The Chemical Rubber Co., Cleveland, 50th edn., page B 3). Examples of such compounds are halides, eg. chlorides and bromides, sulfates, phosphates, nitrates, borates, alcoholates, phenolates, sulfonates, oxides, oxide-hydrates, hydroxides, carboxylates, chelates, carbonates, thiocarbamates and dithiocarbamates. Examples of metals whose compounds can be used are lithium, sodium, potassium, magnesium, calcium, aluminum, tantalum, gallium, tin, lead, bismuth, animony, copper, silver, tungsten, uranium, gold, zinc, mercury, cerium, titanium, vanadium, chromium, molybdenum, manganese, iron, cobalt and nickel. The use of compounds of lithium, calcium, aluminum, tin, bismuth, antimony, copper, zinc, titanium, vanadium, chromium, molybdenum, manganese, iron and cobalt is preferred. The catalysts can also be employed in the form of their hydrates or ammoniates. The amount of catalyst used is advantageously from 0.0001 to 1, preferably from 0.005 to 0.5, especially from 0.01 to 0.1, equivalent of metal cation per mole of carbamic acid ester. The metal compounds can also be employed in a heterogeneous system, bonded to an ion exchanger.

Specific examples of suitable catalysts are lithium methanolate, lithium ethanolate, lithium propanolate, lithium butanolate, sodium methanolate, potassium tert.-butanolate, magnesium methanolate, calcium methanolate, tin-(II) acetate, tin-(II) chloride, tin-(IV) chloride, lead acetate, lead phosphate, antimony-(III) chloride, antimony-(V) chloride, aluminum isobutylate, aluminum trichloride, bismuth-(III) chloride, copper-(II) acetate, copper-(II) sulfate, copper-(II) nitrate, copper molybdate, silver acetate, zinc oxide, zinc chloride, zinc acetate, zinc acetonylacetate, zinc octoate, zinc oxalate, zinc hexanoate, zinc benzoate, zinc undecylenoate, cerium-(IV) oxide, uranyl acetate, titanium tetrabutanolate, titanium tetrachloride, titanium tetraphenolate, titanium naphthenate, vanadium-(III) chloride, vanadium acetonylacetate, chromium-(III) chloride, molybdenum-(IV) oxide, molybdenum acetylacetonate, tungsten-(VI) oxide, manganese-(II) chloride, manganese-(II) acetate, manganese-(III) acetate, iron-(II) acetate, iron-(III) acetate, iron phosphate, iron oxalate, iron-(III) chloride, iron-(III) bromide, cobalt acetate, cobalt chloride, cobalt sulfate, cobalt naphthenate, nickel chloride, nickel acetate and nickel naphthenate and mixtures of these.

The reaction can be carried out as follows: a mixture of the starting materials II and III, with or without the catalyst and/or the solvent, is kept for from 1 to 100 hours at the reaction temperature. At the same time, the ammonia formed is removed from the reaction mixture. The end product is then isolated from the mixture in a conventional manner, for example by fractional distillation.

The isolation is advantageously carried out by stripping the reaction mixture, during the reaction, with gases which are inert under the reaction conditions, and/or with solvent vapors. The gases and vapors extract the ammonia from the reaction mixture and accordingly serve as entraining agents or stripping agents which purify the reaction mixture. In accordance with a definition given in "Introduction to Chemical Engineering" by W. L. Badger and J. T. Banchero (McGraw-Hill Book Comp. Inc. 1955), page 437 (last paragraph), the procedure described will here be referred to as stripping. The inert gases and vapors are as a rule employed in an amount of from 0.01 to 10 mole% per minute, preferably from 0.01 to 0.5 mole% per minute, based on ammonia present in the reaction mixture. Suitable solvents are those which boil below 200° C., preferably from 30° to 140° C. Examples of suitable inert gases are noble gases such as argon and helium, ethane, methane, propane and, preferably, nitrogen and carbon dioxide.

It is also possible to use a proportion of the alcohol III, employed for the reaction, and/or of the solvent, as a stripping agent, and remove an appropriate proportion thereof together with ammonia.

In another preferred embodiment, the carbamic acid ester II is initially prepared, in a first step, from urea and an alcohol of the formula IV $$R^2OH \qquad IV$$

where $R^2$ has the general and preferred meanings given above, by reacting the alcohol IV and urea, advantageously in a molar ratio of from 2 to 50 moles of the former per mole of the latter, for from 1 to 50 hours at from 120° to 230° C., under atmospheric or superatmospheric pressure, continuously or batchwise, in the absence of a solvent or in the presence of a solvent, advantageously one of those mentioned earlier. The reaction according to the invention is then carried out in a second step, using the reaction mixture without isolating the starting material II which has been formed.

The carbonates obtainable by the process of the invention are valuable starting materials for the preparation of dyes, crop protection agents and plastics. Concerning their use, reference may be made to the publications mentioned earlier.

In the Examples, parts are by weight and bear the same relation to parts by volume as that of the kilogram to the liter.

EXAMPLE 1

145 parts of n-hexyl carbamate and 204 parts of hexanol are heated for 20 hours at 180° C. The ammonia formed during the reaction is continuously distilled off, using 1.5 parts by volume of nitrogen per part by volume of reaction mixture per hour as the stripping agent. According to examination by gas chromatography, 27.4 parts of di-n-hexyl carbonate, of boiling point 121°–23° C./4 mbar, are obtained; this is 96.9% of theory, based on converted n-hexyl carbamate. The conversion is 12.2%.

EXAMPLE 2

The procedure described in Example 1 is followed, but additionally 5 parts of p-dimethylaminopyridine are introduced into the reaction mixture. Analysis by gas chromatography shows that over the same period 44.8% of n-hexyl carbamate have been converted and 101 parts of di-n-hexyl carbonate (98.0% of theory, based on converted n-hexyl carbamate) are formed; the product is isolated by subsequent fractional distillation at 121°–23° C./4 mbar.

EXAMPLE 3

6 parts of urea and 39 parts of n-octanol are heated for 5 hours at 130° C., 17.3 parts of n-octyl carbamate being formed from the reactants. A further 39 parts of n-octanol and 0.5 part of tetramethylhexamethylenediamine are then added to the reaction mixture, and the latter is heated for 45 hours at 195° C. The ammonia formed is distilled continuously from the reaction solution, using 2 parts by volume of nitrogen per part by volume of reaction mixture per hour. After completion of the reaction, the reaction mixture is analyzed by gas chromatography and thin layer chromatography. The mixture contains 8.8 parts of n-octyl carbamate and 13.7 parts of di-n-octyl carbonate, corresponding to a conversion of n-octyl carbamate of 49% and a yield of dioctyl carbonate of 97.8%, based on converted n-octyl carbamate.

EXAMPLE 4

131 parts of n-pentyl carbamate, 176 parts of n-pentanol and 5 parts of p-dimethylaminopyridine are heated for 19 hours at 150° C. in a stirred apparatus with distillation attachment, the pressure in the reaction vessel being set to 2–2.5 bar by means of a pressure-regulating valve. The ammonia formed during the reaction is distilled off continuously, using 5 parts by volume of nitrogen per part by volume of reaction mixture per hour. Analysis of the cooled reaction mixture by gas chromatography shows that 36% of the n-pentyl carbamate have been converted and 66.2 parts of di-n-pentyl carbonate (91.0% of theory, based on converted pentyl carbamate), of boiling point 220°–221° C./1 mbar have been formed.

EXAMPLES 5 to 9

The procedure described in Example 4 is followed, but different amines and amidines are used as catalysts. The results of the individual reactions are shown in Table 1 below.

TABLE 1

| Example | Catalyst | Conversion (%) | Yield in % of theory |
|---|---|---|---|
| 5 | diazabicyclo-[2,2,2]-octane | 25 | 92.7 |
| 6 | tetramethylhexamethylene-diamine | 5.5 | 99.3 |
| 7 | N—methylimidazole | 7.6 | 97.9 |
| 8 | diazabicyclo-[4,3,0]-nonene | 50.1 | 92.1 |
| 9 | diazabicyclo-[5,4,0]-undecene | 60.2 | 94.8 |

EXAMPLE 10

The procedure described in Example 4 is followed, but the n-pentanol and n-pentyl carbamate are replaced respectively by isoamyl alcohol and isoamyl carbamate, and diazabicyclo-[4,3,0]-nonene is used as the catalyst. After completion of the reaction, analysis by gas chromatography shows that 66.9% of isoamyl carbamate have been converted and 120.3 parts of diisoamyl carbonate (89% of theory, based on converted isoamyl carbamate), of boiling point 106°–108° C./18 mbar, have been formed.

EXAMPLE 11

14.5 parts of n-hexyl carbamate and 51 parts of hexanol are boiled for 58 hours (200° C./4–5 bar). The ammonia formed during the reaction is distilled off continuously, using 5 parts by volume of nitrogen per part by volume of reaction mixture per hour as the stripping agent. After completion of the reaction, analysis of the reaction solution by gas chromatography shows that 18% of the n-hexyl carbamate have been converted and 4 parts of di-n-hexyl carbonate (96.6% of theory, based on converted n-hexyl carbamate), of boiling point 122°–124° C./4 mbar, have been formed.

EXAMPLE 12

The procedure described in Example 11 is followed, but additionally 0.5 parts of zinc-II acetate is included in the reaction mixture. Analysis by gas chromatography shows that within the same period of time 94% of the n-hexyl carbamate are converted and 20.3 parts of di-n-hexyl carbonate (93.9% of theory, based on converted n-hexyl carbamate), of boiling point 122°–124° C./4 mbar have been formed.

EXAMPLE 13

18 parts of urea and 45 parts of isobutanol are heated for 8 hours at 135° C. in a stirred kettle with distillation attachment, the pressure being set to 2–2.5 bar by means of a pressure-regulating valve. Thereafter, a further 115 parts of isobutanol and 1 part of zinc-II acetate are added, the reaction temperature is raised to 170° C. and the mixture is refluxed for a further 32 hours, the pressure being set to 4–5 bar; the ammonia formed during the reaction is continuously removed from the reaction solution, using 3 parts by volume of nitrogen per liter of reaction mixture per hour as the stripping gas. After completion of the reaction, the mixture is allowed to cool and all the volatile constituents are distilled off under a pressure of 40 mbar. The distillate obtained is then subjected to fractional distillation, giving 106 parts of isobutanol and 48.7 parts of di-isobutyl carbonate (93.3% of theory, based on urea employed), of boiling point 83° C./18 mbar. The conversion of urea is virtually quantitative. The distillation residue still contains 1.1 parts of isobutyl carbamate which can be recycled, so that the yield of di-isobutyl carbonate is 96.3%, based on isobutyl carbamate.

EXAMPLE 14

117 parts of butyl carbamate, 222 parts of butanol and 0.5 part of cobalt acetate are heated in a stirred reactor, the pressure in the reaction vessel being set to 9–10 bar by means of a pressure-regulating valve, so that the boiling point of the reaction mixture is 200° C. The ammonia formed in the reaction is distilled continuously from the reaction solution by means of 3 parts by volume of nitrogen per liter of reaction mixture per hour. After 7 hours, the reaction mixture is cooled and analyzed by gas chromatography. 39.9% of the butyl carbamate employed have been converted; 68.3 parts of dibutyl carbonate (98.4% of theory, based on converted butyl carbamate), of boiling point 97°–98° C./17 mbar, are obtained.

EXAMPLES 15 to 19

The procedure described in Example 14 is followed, but different catalytic compounds are added to the reaction solutions. The results of the individual reactions are shown in Table 2.

EXAMPLES 20 to 25

The procedure described in Example 14 is followed, but instead of butanol and butyl carbamate, different alcohols and carbamates are employed. 0.5 part of manganese acetate is used as a catalyst. The results of the individual reactions are shown in Table 3.

TABLE 2

| Example | Temp. (°C.) | Pressure (bar) | Catalyst | Time (hours) | Molar ratio Starting material II: Starting material III | Conversion (%) | Yield (%) |
|---|---|---|---|---|---|---|---|
| 15 | 210 | 10 | aluminum trichloride | 7 | 1:3 | 34.5 | 92.4 |
| 16 | 210 | 10 | " | 7 | 1:4 | 21.6 | 93.5 |
| 17 | 240 | 14 | tantalum pentachloride | 10 | 1:6 | 92.1 | 73.3 |
| 18 | 210 | 10 | zinc acetate | 9 | 1:8 | 48.4 | 96.1 |
| 19 | 260 | 22 | " | 7 | 1:6 | 76.1 | 87.0 |

TABLE 3

| Example | Temp. (°C.) | Pressure (bar) | Starting materials II and III $R^1$ and $R^2$ = | Time (hours) | Molar ratio Starting material II: Starting material III | Conversion (%) | Yield (%) |
|---|---|---|---|---|---|---|---|
| 20 | 260 | 52 | $C_2H_5$ | 7 | 1:6 | 59.7 | 79.3 |
| 21 | 200 | 22 | " | 7 | 1:6 | 11.6 | 87.6 |
| 22 | 160 | 9 | " | 7 | 1:6 | 4.2 | 75.2 |
| 23 | 180 | 19 | $CH_3$ | 7 | 1:6 | 4.8 | 61.5 |
| 24 | 200 | 29 | " | 7 | 1:6 | 15.4 | 57.0 |
| 25 | 160 | 12 | " | 14 | 1:6 | 2.5 | 93.6 |

We claim:
1. In a process for the preparation of a carbonate of the formula

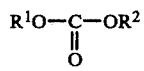

$$R^1O-\underset{\underset{O}{\|}}{C}-OR^2 \qquad I$$

where $R^1$ and $R^2$ are identical or different and each is an aralkyl group of 7 to 12 carbon atoms, an alkenyl group of 2 to 12 carbon atoms, a cycloalkyl group of 5 to 8 carbon atoms or an alkyl group of 1 to 18 carbon atoms, by reacting a carbamic acid ester with an alcohol, the improvement which comprises: reacting a carbamic acid ester of the formula $$H_2N-\underset{\underset{O}{\|}}{C}-OR^2 \qquad \text{II}$$

where $R^2$ has the above meanings, with an alcohol of the formula $$R^1-OH \qquad \text{III}$$

where $R^1$ has the above meanings, at a temperature above 140° C., the ammonia formed being stripped from the reaction mixture during the reaction by passing an inert gas therethrough.

2. A process as claimed in claim 1, wherein the reaction is carried out in the presence of a tertiary amine or amidine as the catalyst.

3. A process as claimed in claim 1, wherein the reaction is carried out in the presence of a catalytic amount of a compound of a metal chosen from the elements of groups Ia, Ib, IIa, IIb, IIIa, IIIb, IVa, IVb, Va, Vb, VIb, VIIb and VIIIb of the periodic table.

4. A process as claimed in claim 1, wherein the reaction is carried out with from 0.9 to 50 moles of starting material III per mole of starting material II.

5. A process as claimed in claim 1, wherein the reaction is carried out at from 140° to 260° C.

6. A process as claimed in claim 1, wherein the reaction is carried out at from 140° to 230° C.

7. A process as claimed in claim 1, wherein the reaction is carried out under a pressure of from 0.1 to 60 bar.

8. A process as claimed in claim 1, wherein the reaction is carried out in the presence of a solvent which is inert under the reaction conditions and in which ammonia is only sparingly soluble.

9. A process as claimed in claim 1, wherein the reaction is carried out using as the stripping medium an inert gas in an amount of 0.01–10 mole% per minute, based on ammonia present in the reaction mixture.

10. A process as claimed in claim 1, wherein the reaction is carried out in the presence of a tertiary amine or amidine as a catalyst having from 0.0001 to 1 equivalent of amino or amidine group in the molecule of the catalyst, per mole of starting material II.

11. A process as claimed in claim 1, wherein the reaction is carried out with from 0.0001 to 1 equivalent of a compound of a metal selected from the elements of groups Ia, IB, IIa, IIb, IIIa, IIIb, IVa IVb, Va, Vb, VIb, VIIb and VIIIb of the periodic table as a catalyst, providing from 0.0001 to 1 equivalent of metal cation per mole of carbamic acid ester.

12. A process as claimed in claim 1 wherein nitrogen is used as the inert stripping gas.

* * * * *

UNITED STATES PATENT AND TRADEMARK OFFICE
CERTIFICATE OF CORRECTION

PATENT NO. : 4,436,668
DATED : March 13, 1984
INVENTOR(S) : Wolfgang Harder, Franz Merger, Friedrich Towae It is certified that error appears in the above-identified patent and that said Letters Patent is hereby corrected as shown below:

On the first page, after line [22] and before line [51], insert the lines:

-- [30]  Foreign Application Priority Data

June 7, 1980 [DE] Fed. Rep. of Germany ... 3021554 --

Signed and Sealed this

Eleventh Day of September 1984

[SEAL]

Attest:

GERALD J. MOSSINGHOFF

Attesting Officer    Commissioner of Patents and Trademarks